(12) United States Patent
Eidenschink

(10) Patent No.: US 8,377,038 B2
(45) Date of Patent: Feb. 19, 2013

(54) MEDICAL DEVICES INCLUDING SHAPE MEMORY MATERIALS

(75) Inventor: Tracee Eidenschink, Wayzata, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 13/271,085

(22) Filed: Oct. 11, 2011

(65) Prior Publication Data

US 2012/0035592 A1 Feb. 9, 2012

Related U.S. Application Data

(63) Continuation of application No. 11/403,615, filed on Apr. 13, 2006, now Pat. No. 8,034,046.

(51) Int. Cl.
*A61M 25/00* (2006.01)

(52) U.S. Cl. .................. 604/531; 604/524; 604/530

(58) Field of Classification Search .................. 604/19, 604/264, 523, 524, 528, 530–532
See application file for complete search history.

(56) References Cited

U.S. PATENT DOCUMENTS

| | | | |
|---|---|---|---|
| 5,342,307 A | 8/1994 | Euteneuer et al. |
| 5,350,361 A | 9/1994 | Tsukashima et al. |
| 5,456,666 A | 10/1995 | Campbell et al. |
| 5,458,572 A | 10/1995 | Campbell et al. |
| 5,490,839 A | 2/1996 | Wang et al. |
| 5,662,621 A | 9/1997 | Lafontaine |
| 5,738,901 A | 4/1998 | Wang et al. |
| 6,013,055 A | 1/2000 | Bampos et al. |
| 6,090,072 A | 7/2000 | Kratoska et al. |
| 6,123,718 A | 9/2000 | Tu et al. |
| 6,249,076 B1 | 6/2001 | Madden et al. |
| 6,323,459 B1 | 11/2001 | Maynard |
| 6,388,043 B1 | 5/2002 | Langer et al. |
| 6,514,237 B1 | 2/2003 | Maseda |
| 6,679,836 B2 | 1/2004 | Couvillon, Jr. |
| 6,720,402 B2 | 4/2004 | Langer et al. |
| 6,749,556 B2 | 6/2004 | Banik |
| 6,872,433 B2 | 3/2005 | Seward et al. |
| 6,921,360 B2 | 7/2005 | Banik |
| 7,353,747 B2 | 4/2008 | Swayze et al. |
| 7,371,223 B2 | 5/2008 | Couvillon, Jr. et al. |
| 2003/0236445 A1 | 12/2003 | Couvillon, Jr. |
| 2004/0068220 A1 | 4/2004 | Couvillon, Jr. et al. |
| 2004/0087982 A1 | 5/2004 | Eskuri |
| 2004/0230090 A1 | 11/2004 | Hegde et al. |

(Continued)

FOREIGN PATENT DOCUMENTS

| | | |
|---|---|---|
| DE | 103 57 743 | 1/2005 |
| WO | 86/03980 | 7/1986 |

(Continued)

OTHER PUBLICATIONS

Sterlz, Tobias et al., "Bistable shape memory thin film actuators," Smart Structures and Materials 2003: Active Materials: Behavior and Mechanics, Proceedings of SPIE vol. 5053 (2003) pp. 101-109.

(Continued)

*Primary Examiner* — Victoria P Shumate
(74) *Attorney, Agent, or Firm* — Seager, Tufte & Wickhem, LLC

(57) ABSTRACT

Medical devices, such as catheters, including shape memory materials, are provided, as well as related methods of making and using such medical devices.

19 Claims, 12 Drawing Sheets

U.S. PATENT DOCUMENTS

| | | |
|---|---|---|
| 2005/0004425 A1 | 1/2005 | Banik |
| 2005/0075625 A1 | 4/2005 | Dao et al. |
| 2005/0102017 A1 | 5/2005 | Mattison |
| 2005/0165439 A1 | 7/2005 | Weber et al. |
| 2006/0129232 A1 | 6/2006 | Dicarlo et al. |
| 2006/0206140 A1 | 9/2006 | Shaolian et al. |
| 2007/0112331 A1 | 5/2007 | Weber et al. |
| 2008/0009831 A1* | 1/2008 | Griffin .......................... 604/531 |
| 2010/0116279 A9* | 5/2010 | Cooper ........................ 128/898 |

FOREIGN PATENT DOCUMENTS

| | | |
|---|---|---|
| WO | 90/11793 | 10/1990 |
| WO | 94/19051 | 9/1994 |
| WO | 2006/060312 | 6/2006 |

OTHER PUBLICATIONS

Liu, Yiping et al., "Thermomechanics of shape memory polymer nanocompposites," Mechanics of Materials 36 (2004) pp. 929-940.

* cited by examiner

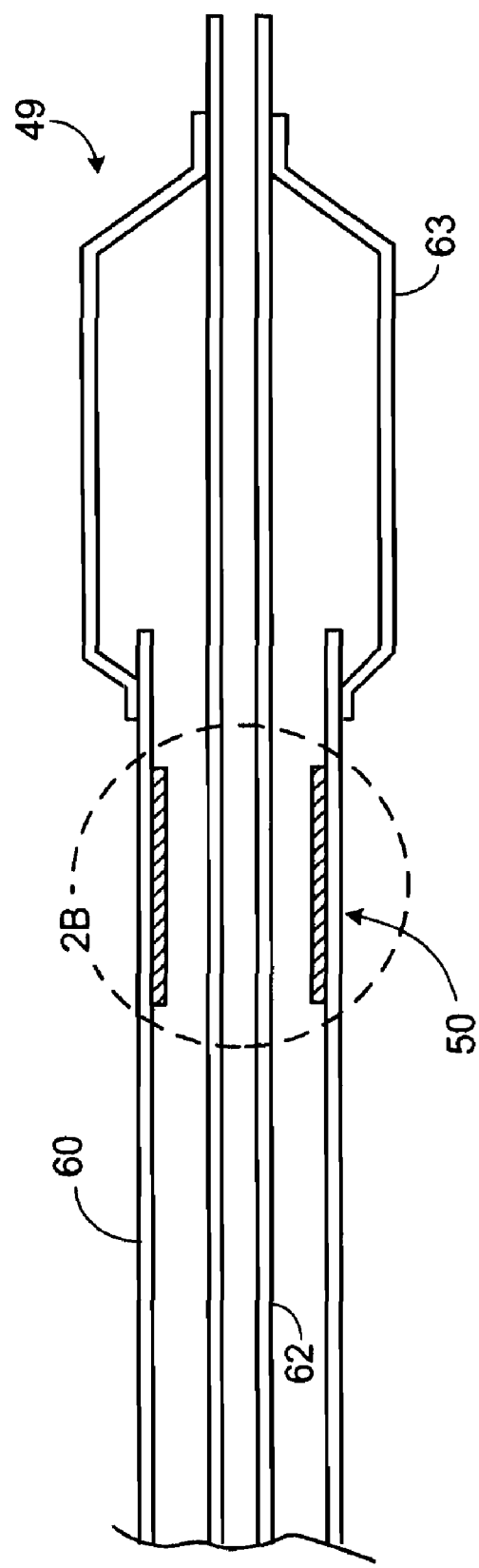

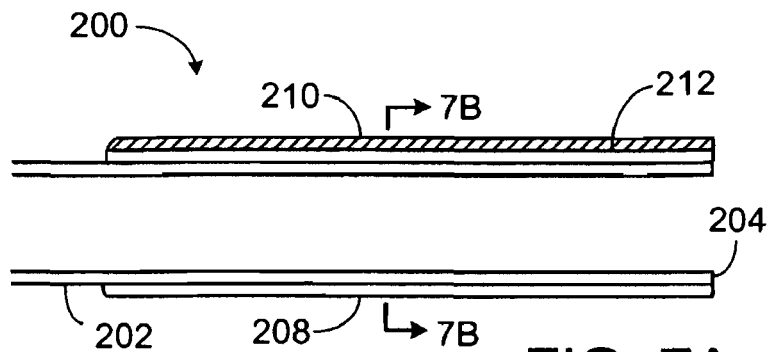
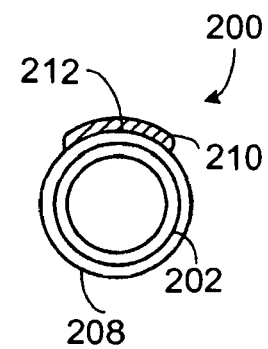
FIG. 7A  FIG. 7B
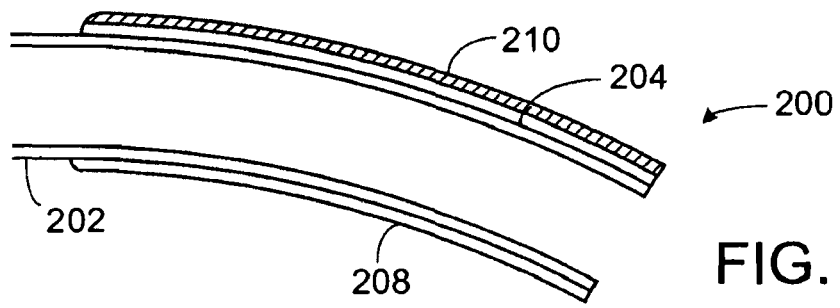
FIG. 7C
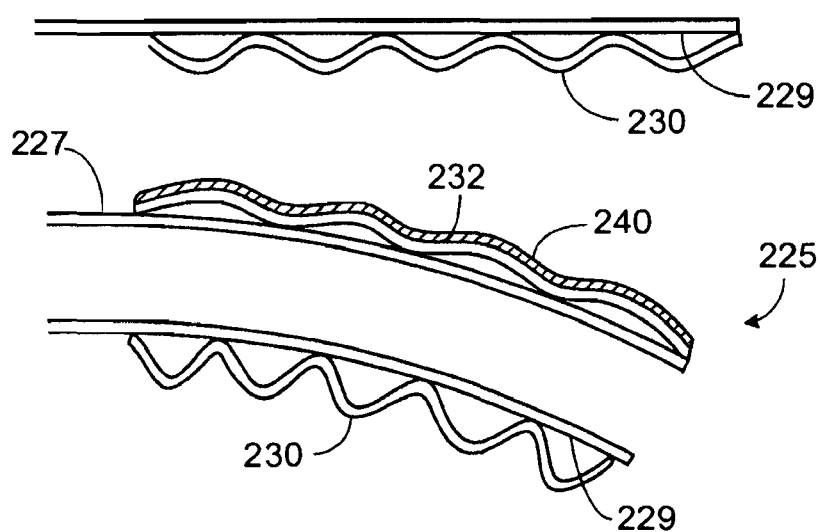
FIG. 8A
FIG. 8B

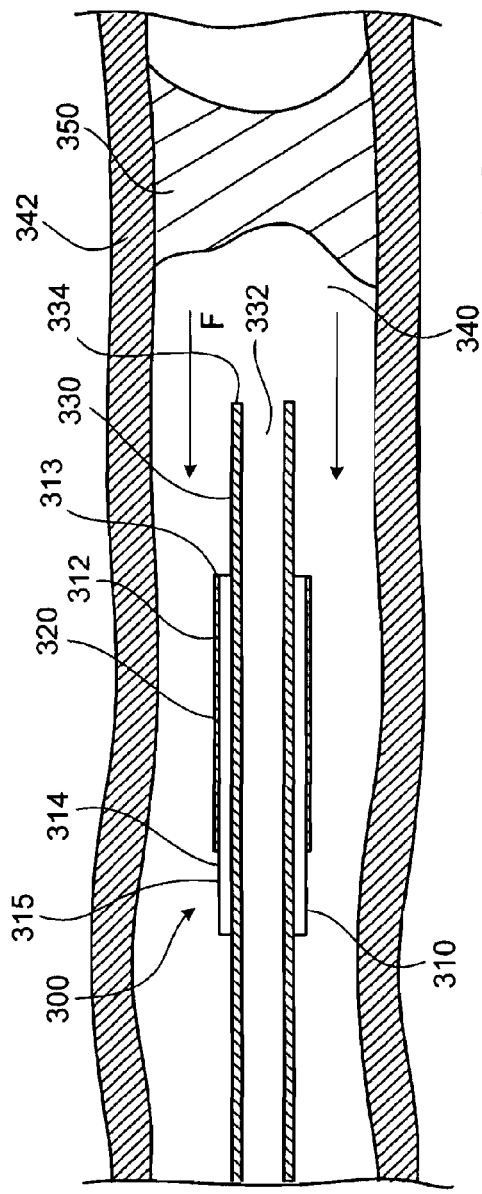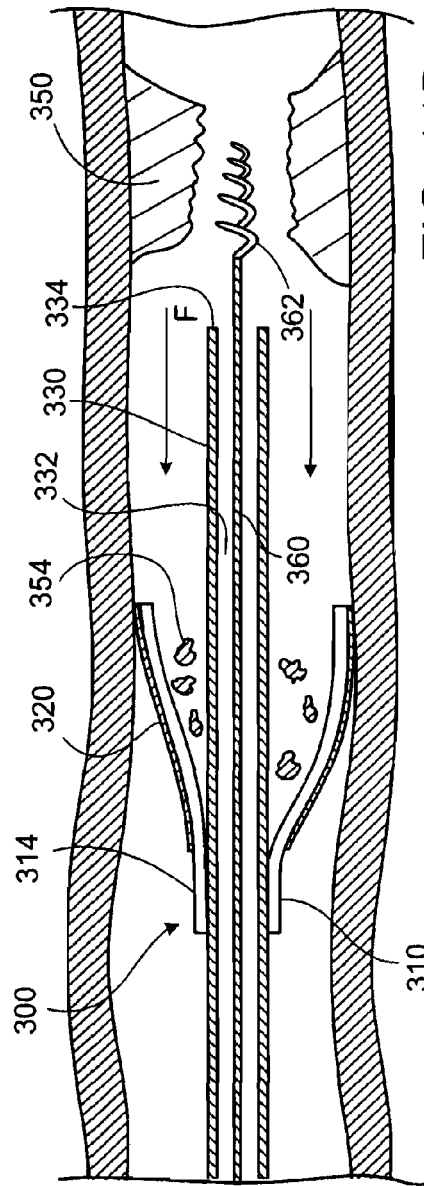

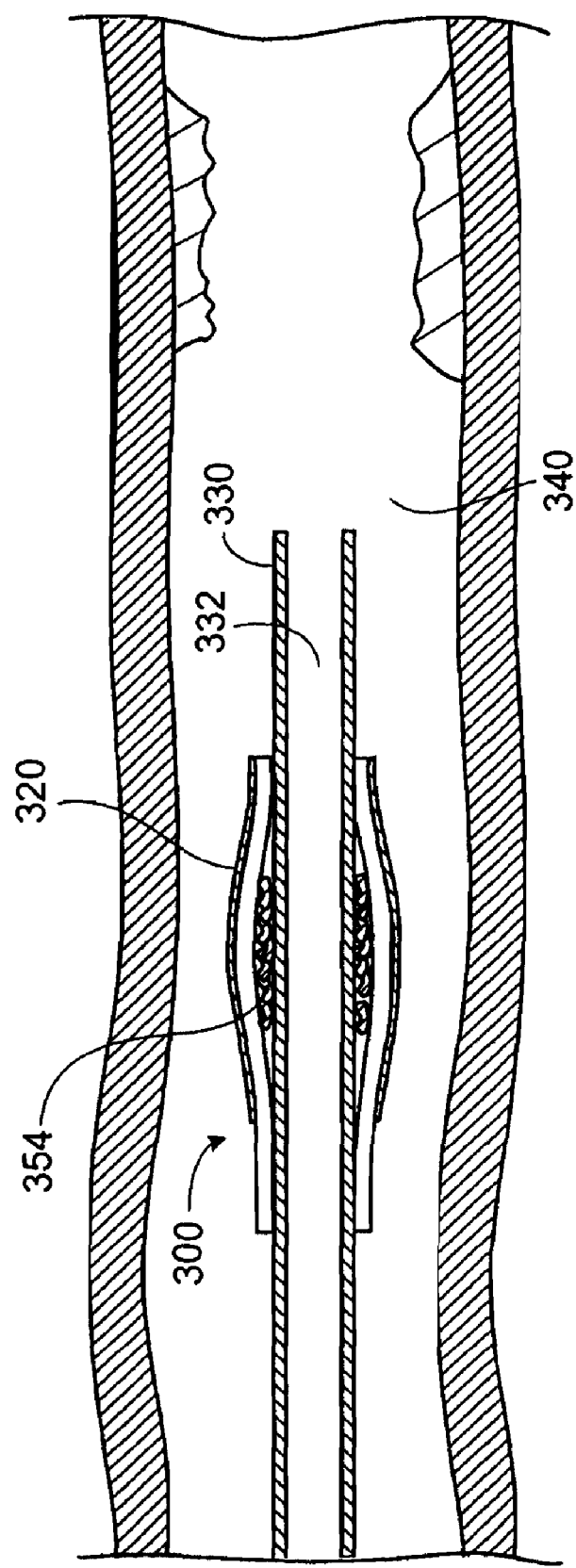

MEDICAL DEVICES INCLUDING SHAPE MEMORY MATERIALS

CROSS-REFERENCE TO RELATED APPLICATIONS

The present application is a continuation of co-pending U.S. application Ser. No. 11/403,615, filed Apr. 13, 2006; the entire disclosures of which are all incorporated herein by reference.

TECHNICAL FIELD

The invention relates to medical devices, such as catheters, including shape memory materials.

BACKGROUND

Intravascular medical devices such as, for example, guide wires, catheters, and medical tubing, allow physicians to perform a medical procedure, such as angioplasty or delivery of a stent. In some cases, a device is inserted into a patient's vascular system at a convenient site and subsequently delivered, e.g., pushed, through the vascular system to a target site. The path that the device takes through the vascular system to the target site can be relatively tortuous, for example, requiring the device to change direction frequently.

In some circumstances, it is desirable for the device to have relatively good trackability so that it can travel along the tortuous path. At the same time, the device preferably has good pushability so that forces applied proximally to the device can be transmitted distally to deliver the device.

SUMMARY

In one aspect, medical devices are provided that have one or more sections that include a shape memory polymer. The shape memory polymer has a conductive layer on portions thereof. The portions of shape memory polymer that have a conductive layer thereon can be activated by energizing (e.g., applying electrical current or heat to) the conductive layer, at which point these portions can change shape, while the remainder of the shape memory polymer is unactivated and remains in its original shape.

The ability to selectively activate portions of the shape memory polymer can be utilized for a number of purposes. For example, a locking sleeve of shape memory polymer can be located between an inner and an outer member of a dual-member catheter. The locking sleeve can, in an unactivated state, contact only one of the members, and once the portions having a conductive layer thereon are activated, these portions can change shape to contact the other member such that the outer and inner members are locked to one another, increasing the stiffness of the catheter.

As another example, a catheter can include a shape memory polymer at its distal end. The shape memory polymer can have a conductive layer on a portion that does not extend around the periphery of the member, such that, once activated, the activated portion changes shape (e.g., lengthens) to steer the catheter in a direction opposite the lengthened portion.

As still another example, a lumen filter system can include a shape memory polymer sleeve surrounding a tubular member. The shape memory polymer sleeve can include holes (e.g., can be mesh-like) and can have a conductive layer on a distal portion. When unactivated, the shape memory polymer sleeve lays against the tubular member. When activated, the distal portion can expand (e.g., to press against or into a lumen wall) while the proximal end of the shape memory polymer sleeve continues to lay against the tubular member. The shape memory polymer sleeve can thus function to filter fluid passing through the lumen, catching debris passing therethrough. When desired, the energy supplied to the conductive layer can be turned off, deactivating the distal portion of the shape memory polymer, which can then return to its original position, laying against the tubular member. This can effectively entrap the filtered material, retaining such material against the tubular member and allowing for its removal, along with the tubular member, from the lumen.

In another aspect, medical devices are provided that include a shape memory polymer having a conductive material, that is not a shape memory material, on at least a portion thereof.

In another aspect, catheters are provided, the catheters having a distal portion including a shape memory polymer. A conductive material is on at least a portion of a surface of the shape memory polymer.

In still another aspect, catheters are provided. The catheters include an outer member, an inner member, and a structure located between the outer and inner members. The structure includes a shape memory polymer and a conductive material on the shape memory polymer.

Embodiments can include one or more of the following features.

The conductive material can be configured to activate less than 100% (e.g., less than 50%) of the shape memory polymer. The conductive material can extend over less than the full length of the shape memory polymer. The conductive material can extend over less than the full perimeter of the shape memory polymer.

The shape memory polymer can have multiple (e.g., two, three, four, five or more) sections that have a conductive layer thereon. The multiple sections of conductive layer can be connected (e.g., electrically connected) such that each can be activated from the same energy source. The multiple sections can be unconnected, with each section separately connected to an energy source, for example, such that one or more sections can be energized independently of one or more other sections.

The shape memory polymer can be configured to change its shape, size, and/or dimensions upon being activated. The shape memory polymer can be configured to expand to a larger diameter when activated. The shape memory polymer can be configured to change from a generally corrugated configuration to a generally uncorrugated configuration (or vice versa) when activated. The shape memory polymer can be configured to contact one of an inner and outer member when unactivated and to contact the other of the inner and outer member when activated.

Embodiments can include one or more of the following advantages. The devices permit the selection by the physician of having the catheters be locked, providing greater rigidity and pushability, or unlocked, permitting greater flexibility of the catheters. The devices permit steering of a catheter, in that the tip of the catheter can be alternatingly bent or curved and straightened. Embodiments permit activation of multiple portions or areas of shape memory polymer utilizing a single wire, reducing the complexity and/or size of the system. By applying the conductive layer to predetermined portions, various different configurations can be created in the sleeve to achieve a variety of purposes. Advantageously, the sleeves can be cheaply and rapidly produced, e.g., by forming the sleeve out of substantially pure shape memory polymer, and various inexpensive, accurate and fast techniques can be used to apply the conductive layer to achieve precise activated configurations.

The details of one or more embodiments of the invention are set forth in the accompanying drawings and the description below. Other aspects, features, and advantages will be apparent from the description and drawings, and from the claims.

DESCRIPTION OF DRAWINGS

FIG. 2A is a cross-sectional view of an embodiment of a balloon catheter including a shape memory polymer.

FIG. 7A is a detailed, cross-sectional view of an embodiment of a catheter including a shape memory polymer in a first state; FIG. 7B is a cross-sectional view of the catheter of FIG. 7A, taken along line 7B-7B; and FIG. 7C is a cross-sectional view of the catheter of FIG. 7A, with the shape memory polymer in a second state.

FIG. 8A is a detailed, cross-sectional view of an embodiment of a catheter including a shape memory polymer in a first state; and FIG. 8B is a cross-sectional view of the catheter of FIG. 8A, with the shape memory polymer in a second state.

FIGS. 11A, 11B, and 11C are cross-sectional views of an embodiment of a lumen filter system during use in a body vessel.

DETAILED DESCRIPTION

The invention features structures that have one or more portions including a shape memory material, which can be selectively activated to assume one or more predetermined shapes.

Figure 1A:
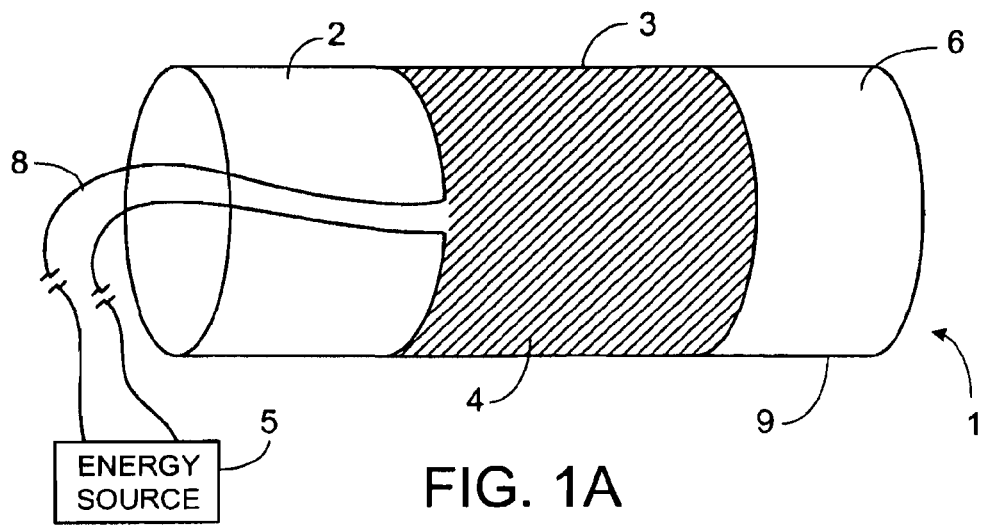
FIG. 1A is a perspective view of an embodiment of a sleeve including a shape memory polymer in a first state.
Figure 1B:
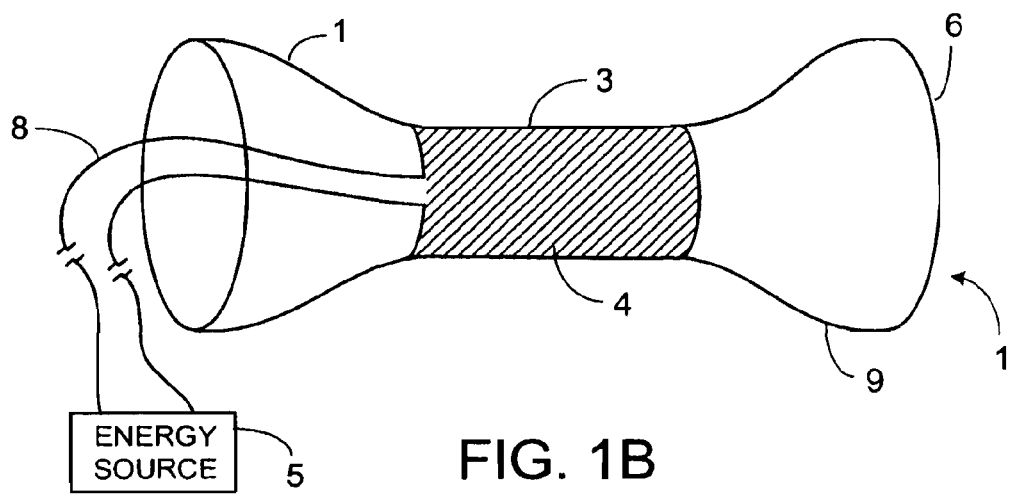
FIG. 1B is a perspective view of the shape memory polymer of FIG. 1A in a second state.

Referring to FIGS. 1A and 1B, a shape memory polymer ("SMP") structure (as shown, a sleeve 1) includes a tubular member 9 and a conductive layer or coating 4 (e.g., gold) applied to an exterior first portion 3 of the tubular member. Tubular member 9 includes (e.g., is formed of) a shape memory polymer (e.g., polycyclooctene) that is capable of transitioning from a first shape to a second, predetermined shape upon exposure to a stimulus, such as heat. Tubular member 9 further includes a second portion 2 and a third portion 6 on which conductive layer 4 is not applied. Conductive layer 4 is connected by wires 8 to an energy source 5 (such as a constant current source) that is capable of delivering energy to the conductive layer. The energy is capable of heating conductive layer 4, which in turn can heat first portion 3 of tubular member 9 to change the shape memory polymer from the first shape (FIG. 1A) to the second shape FIG. 1B). Second portion 2 and third portion 6, which do not include conductive layer 4, do not substantially change in shape. Thus, tubular member 9 includes a selected portion (or portions as described below) configured to change shape selectively, and one or more portions that does not change shape. By applying conductive layer 4 to predetermined portions, various configurations can be created to achieve a variety of purposes. As described below, structures, such as sleeve 1, can be applied to medical devices to enhance the performance of the devices. For example, the shape memory polymer structures can be utilized as locking devices for catheters, in steering mechanisms for steering catheters through a tortuous vessel anatomy, and in filters for filtering fluids in body lumens.

Locking Devices

Figure 2B:
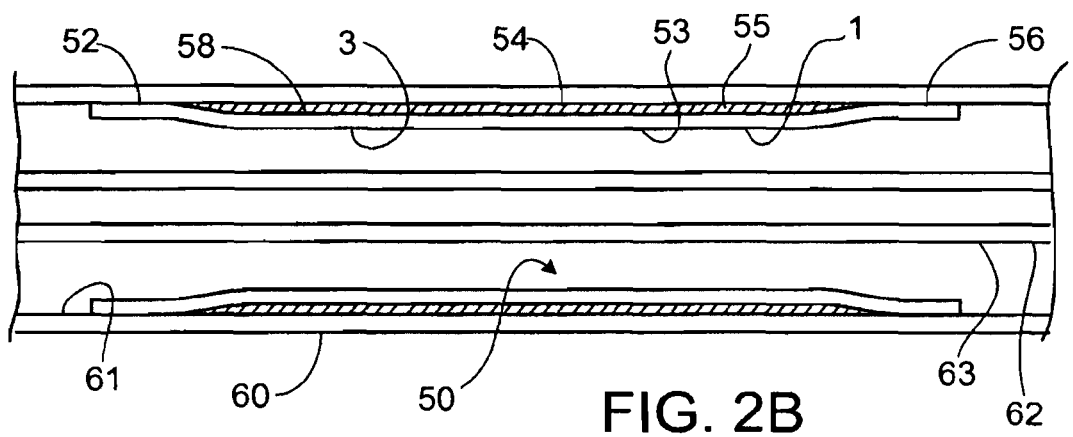
FIG. 2B is a detailed view of the balloon catheter of FIG. 2A, with the shape memory polymer in a first state.
Figure 2C:
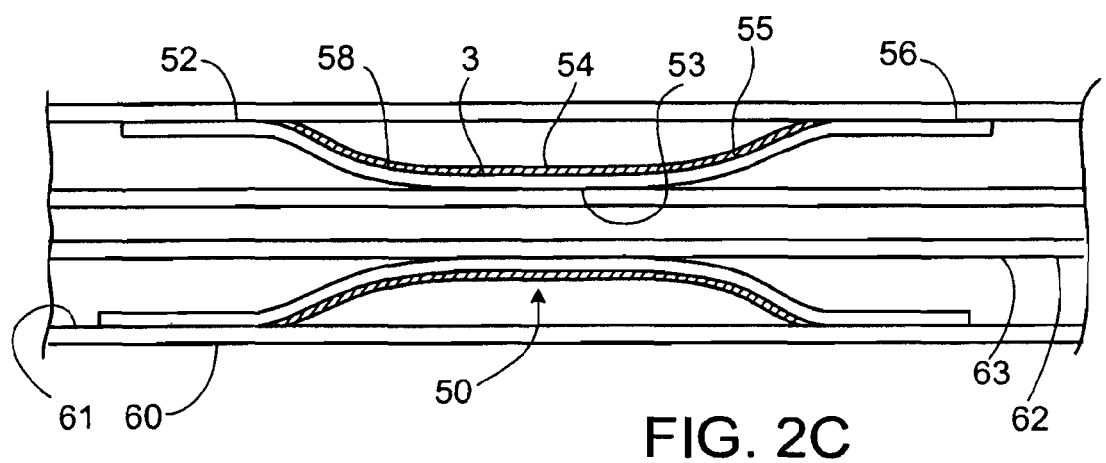
FIG. 2C is a detailed view of the balloon catheter of FIG. 2A, with the shape memory polymer in a second state.

FIGS. 2A, 2B, and 2C show a balloon catheter 50 including sleeve 1, which serves as a mechanism to selectively change the stiffness of the balloon catheter. Balloon catheter 50 includes an outer member 60, an inner member 62 at least partially surrounding the outer member, and an expandable balloon 63 carried by outer and inner members 60, 62. As shown, sleeve 1 is secured to outer member 60 (e.g., by laser bonding or adhesive bonding) proximally of balloon 63 and between outer and inner members 60, 62. Sleeve 1 can in certain embodiments have a diameter sufficiently large to form an interference fit within outer member 60 and not require bonding to the outer member 60. Conductive layer 4 of sleeve 1 is in an electrical communication with energy source 5 (not shown) by wires (not shown). The wires can extend proximally between the outer and inner members 60, 62 and/or be embedded in one or both of the outer and inner members 60, 62.

Sleeve 1 is capable of changing from a first shape to a second shape to change the rigidity of balloon catheter 50. More specifically, referring to FIG. 2B, in a first, unlocked shape, an exterior surface 58 of sleeve 1 abuts an interior surface 61 of outer member 60, and the sleeve does not contact inner member 62. Outer and inner members 60, 62 are uncoupled, and balloon catheter 50 is relatively flexible so that it can track a tortuous path. Referring to FIG. 2C, upon exposing conductive layer 4 to energy, the shape memory polymer of first portion 3 changes to a second, predetermined shape in which the polymer reduces in diameter until an interior surface 53 of first portion 3 firmly contacts an exterior surface 63 of inner catheter 62. As a result, sleeve 1 couples or locks the outer member 60 to the inner member 62 and reduces movement of the outer member relative to the outer member. Locking outer and inner members 60, 62 together reinforces them and makes balloon catheter 50 more rigid and enhances the pushability of the balloon catheter, which is useful, for example, when the balloon catheter is pushed through a narrow opening. Thus, sleeve 1 allows the rigidity of balloon catheter 50 to be selectively changed.

In some embodiments, to enhance the coupling or locking between outer and inner members 60, 62, the materials for tubular member 9 and/or inner member 62 are selected to increase friction between the tubular member 9 and the inner member 62. Examples of high friction materials include low durometer nylons, urethanes, and polyether block amides (e.g., PEBAX® polymers). The tubular member 9 and/or the inner member 62 can be formed of the high friction materials, and/or the high friction materials can be coated on one or more contact surfaces of the tubular member 9 and/or the inner member 62.

Figure 3A:
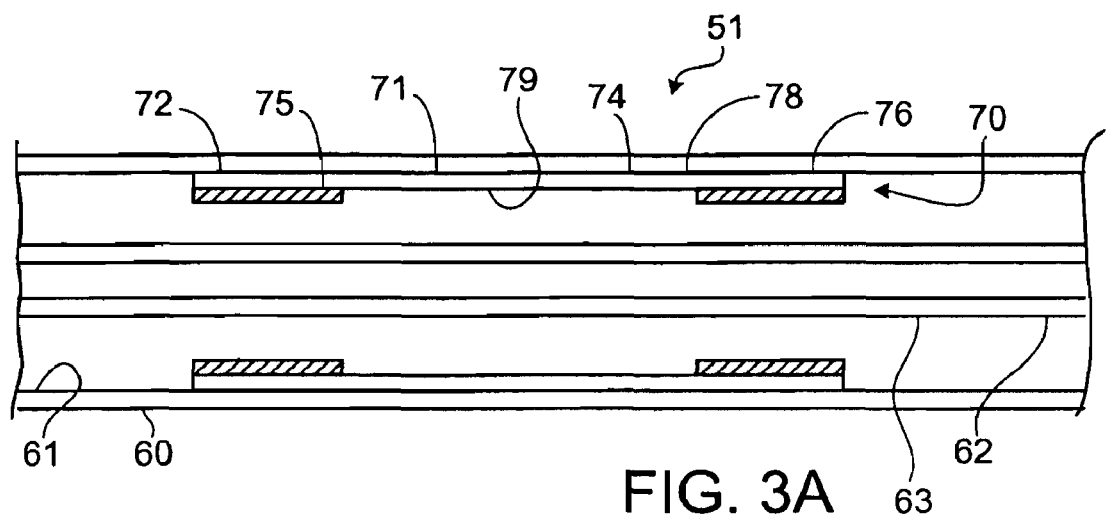
FIG. 3A is a detailed, cross-sectional view of an embodiment of a balloon catheter including a shape memory polymer in a first state.
Figure 3B:
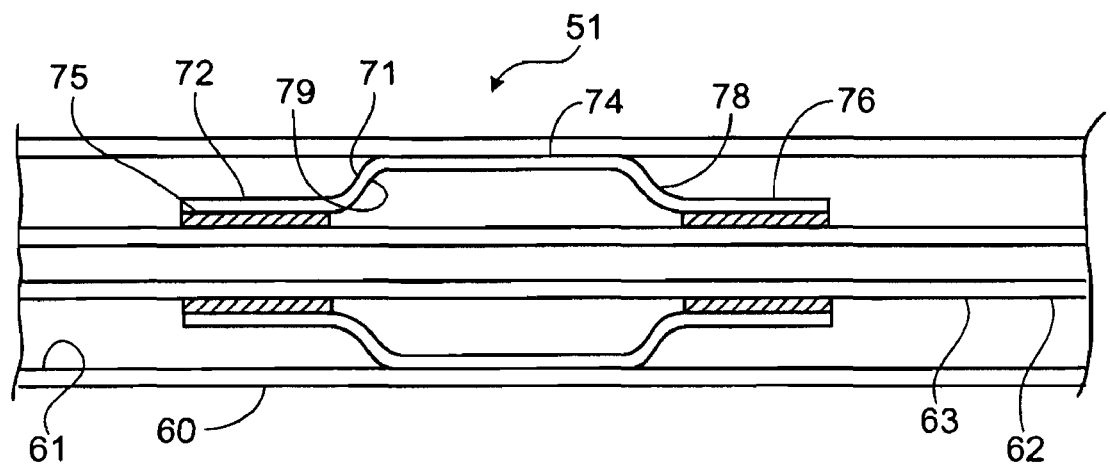
FIG. 3B is a cross-sectional view of the balloon catheter of FIG. 3A, with the shape memory polymer in a second state.

In other embodiments, the SMP structure is configured to have a conductive layer applied to more than one portion so that more than one portion can selectively change shape. For example, FIGS. 3A and 3B show a sleeve 70 in a balloon catheter 51 similar to catheter 50. Sleeve 70 includes an SMP tubular member 71 having a first portion 72, a second portion 74, and a third portion 76. Second portion 74 is secured to outer member 60. Sleeve 70 further includes a conductive layer 75 on an interior surface 79 of first and third portions 72, 76. In a first, unlocked position, an exterior surface 78 of sleeve 70 abuts an interior surface 61 of outer member 60, and the sleeve does not contact inner member 62. Upon activation via conductive layer 75, the shape memory polymer of first and third portions 72, 76 changes shape and reduces in diameter until the conductive layer 75 contacts exterior surface 63 of inner member 62, thereby locking outer and inner members 60, 62 and enhancing the rigidity of the balloon catheter 51.

Figure 4A:
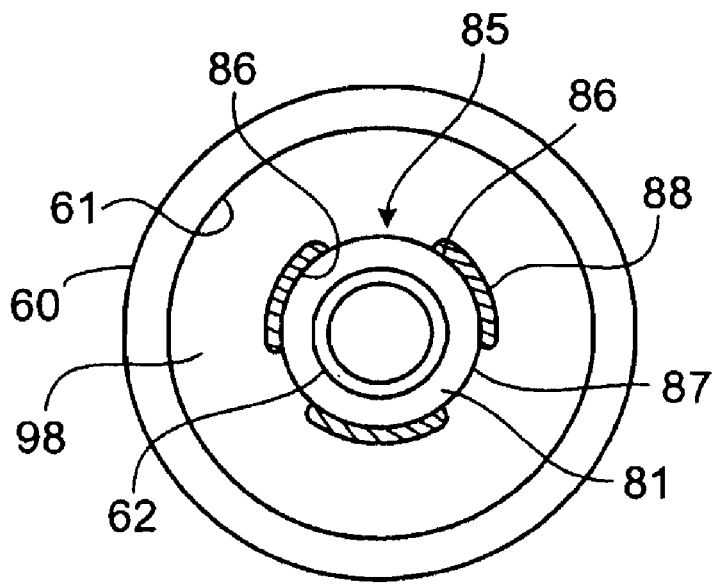
FIG. 4A is a detailed, cross-sectional view of an embodiment of a balloon catheter including a shape memory polymer in a first state.
Figure 4B:
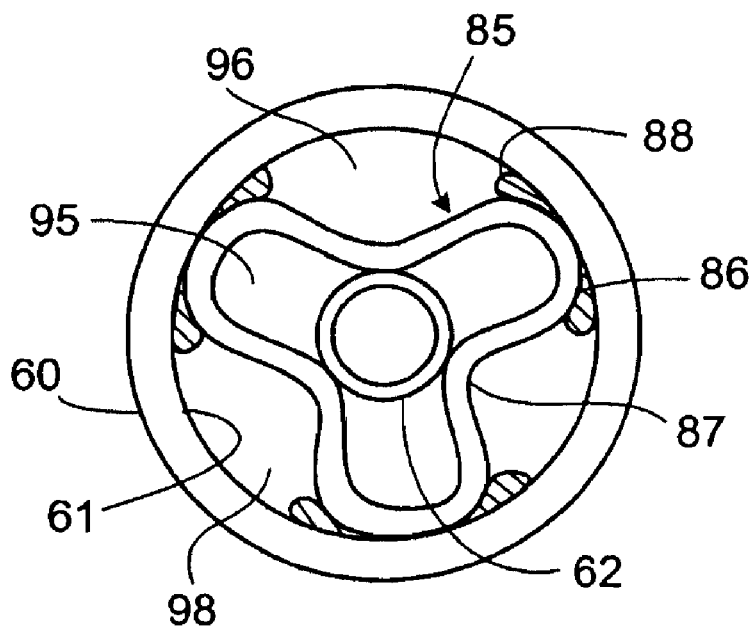
FIG. 4B is a cross-sectional view of the balloon catheter of FIG. 4A, with the shape memory polymer in a second state.

While sleeves 1, 70 have a conductive layer that extends completely around the perimeter of the sleeves, in other embodiments, the conductive layer does not extend completely around the perimeter of the sleeve. FIGS. 4A and 4B show a sleeve 85 in a balloon catheter similar to catheter 49. Sleeve 85 includes an SMP tubular member 81 and multiple conductive layers 88 extending longitudinally on selected first portions 86 of the tubular member. Conductive layers 88 are spaced from each other along the perimeter of sleeve 85, so tubular member 81 includes second portions 87 extending longitudinally that do not have conductive material thereon. Second portions 87 are secured to the inner member 62. In a first, unlocked position, sleeve 85 is adjacent to and in contact with the inner member 62 (FIG. 4A). When energy is provided to conductive layers 88, the shape memory polymer of first portions 86 is activated and expands to contact the interior surface 61 of the outer member 60 (FIG. 4B), thereby locking the outer and inner members 60, 62 to one another while leaving channels 95, 96 for fluid to pass longitudinally through a lumen 98 between the outer and inner members 60, 62.

Figure 5A:
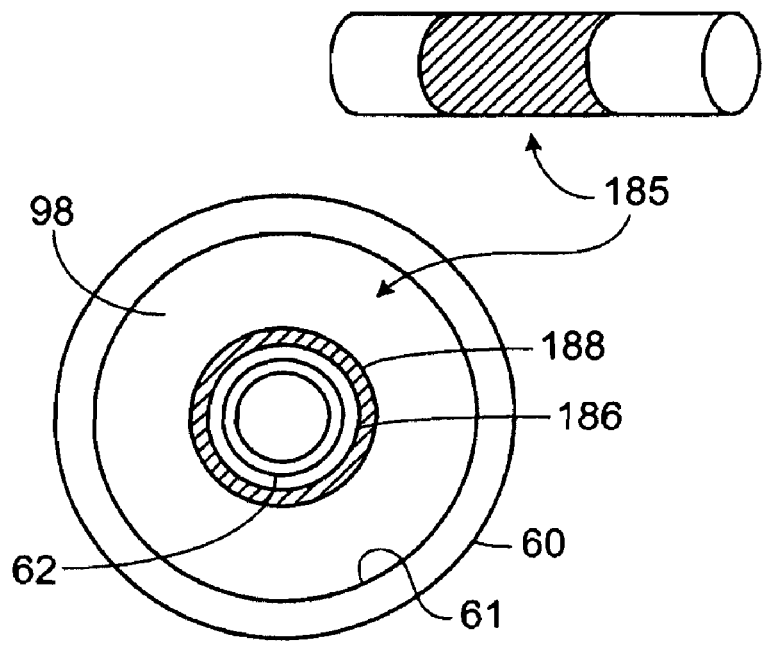
FIG. 5A is a detailed, cross-sectional view of an embodiment of a balloon catheter including a shape memory polymer in a first state.
Figure 5B:
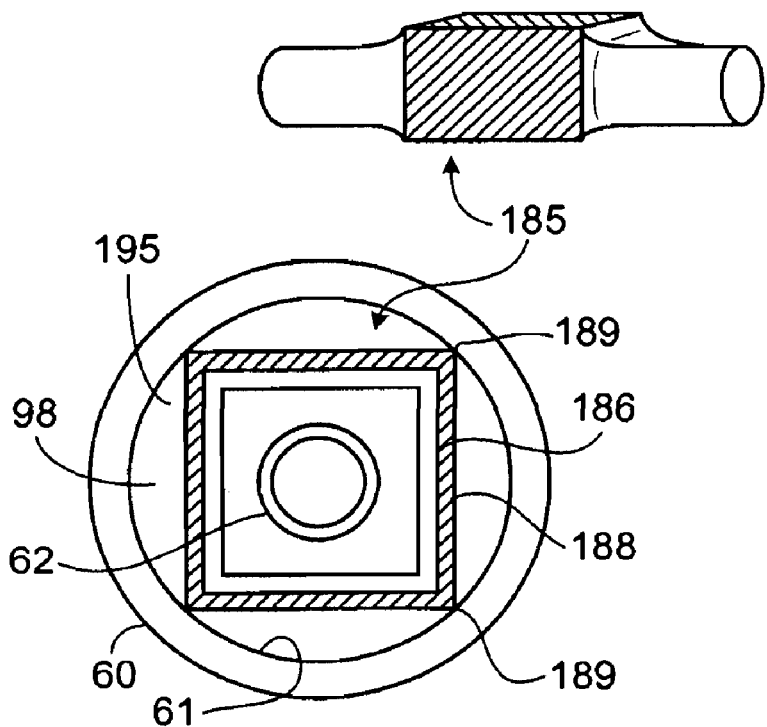
FIG. 5B is a cross-sectional view of the balloon catheter of FIG. 5A, with the shape memory polymer in a second state.

The SMP structures can change to other shapes. For example, FIGS. 5A and 5B show an SMP sleeve 185 having first portions 186 extending circumferentially around the sleeve and a conductive layer 188 on the first portions. SMP sleeve 185 is configured to assume a polygonal cross-sectional shape (as shown, a square-shaped cross section) upon activation, with the corners 189 contacting the interior surface 61 of outer catheter 60. Other portions of sleeve 185 having no conductive material thereon remain in contact with inner catheter 62. As a result, sleeve 185 is capable of locking the outer and inner members 60, 62 together while leaving channels 195 for fluid to pass longitudinally through lumen 198 between the outer and inner members 60, 62.

Figure 6A:
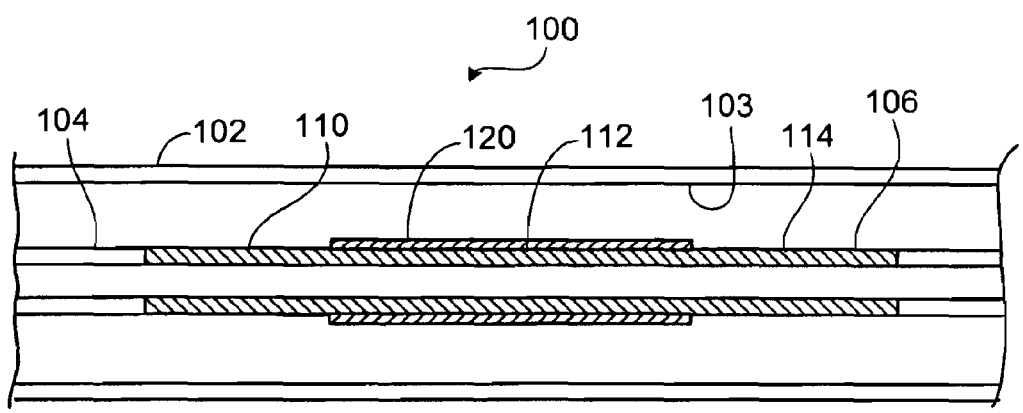
FIG. 6A is a detailed, cross-sectional view of an embodiment of a balloon catheter including a shape memory polymer in a first state.
Figure 6B:
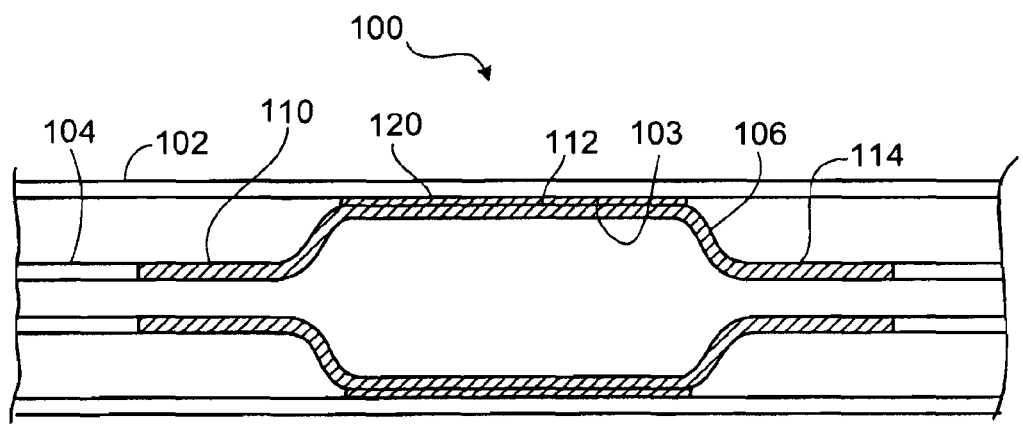
FIG. 6B is a cross-sectional view of the balloon catheter of FIG. 6A, with the shape memory polymer in a second state.

In other embodiments, the inner member and/or the outer member includes a section having shape memory polymer and a conductive coating that permits locking of the inner and outer members to each other without the need for a separate sleeve. FIGS. 6A and 6B illustrate a catheter system 100 which includes an outer member 102 and an inner member 104. Inner member 104 has a locking section 106 that includes a shape memory polymer. Locking section 106 has a first portion 110, a second portion 112, and a third portion 114. Second portion 112 has a conductive layer 120 thereon. When not activated, inner member 104 exhibits a standard tubular shape and does not contact outer member 102. When energy is provided to the conductive layer 120, the shape memory polymer of the second portion 112 is activated and expands to contact an inner surface 103 of the outer member 102, thereby locking the inner and outer members 102, 104 to each other in a similar fashion to that described above. Alternatively or additionally, the outer member 102 can include an SMP portion with a conductive layer that is capable of moving inwardly to contact the inner member 104.

Still other embodiments can be formed. For example, an SMP sleeve can have two portions, one of which can contact the inner surface of an outer member when activated and the other of which can contact the outer surface of an inner member when activated. In certain embodiments, an SMP sleeve can include multiple portions (e.g., three, four, five, six, seven, eight, nine, or ten or more portions) in which alternating portions have a conductive layer applied thereto, such that, upon activation, each member is contacted at a number of points to increase the radial rigidity of the catheter and to maintain the catheter in a non-collapsed configuration against inwardly-directed radial pressure.

The shape memory polymer sleeves can have a range of sizes. For example, the sleeve in a collapsed position (e.g., a first shape) can, e.g., have a length L1 from about 3 mm to about 75 mm, an outer diameter OD1 from about 0.1 mm to about 20 mm, and a wall thickness W1 of from about 0.002 mm to about 1.0 mm. Depending on the application, the activated portions of the shape memory polymer sleeve in an expanded position (e.g., a second shape) can, e.g., have an outer diameter OD2 from about 1.2 ×OD1 to about 3 ×OD1, and a wall thickness W2 from about 0.5 ×W1 to about 0.9 ×W1. As described below, in some embodiments, after further expansion, a segment of the shape memory polymer sleeve in a second expanded position (e.g., a third shape) can, e.g., have an outer diameter OD3 from about 1.2×OD2 to about 3 ×OD2, and a wall thickness W3 from about 0.5×W2 to about 0.9×W2.

Steering Sleeves

Structures including shape memory polymer having conductive layers capable of activating selected part(s) of the shape memory polymer can also be used to form steerable catheters. FIGS. 7A and 7B show a steerable catheter 200 including a member 202 having a distal portion 204. A shape memory polymer sleeve 208 surrounds the distal portion 204 of member 202. As shown, a conductive layer 210 overlays (e.g., coats) a segment 212 of shape memory polymer sleeve 208 that extends longitudinally for substantially the length of the shape memory polymer sleeve 208 and extends circumferentially around only a portion of shape memory polymer sleeve 208. Conductive layer 210 is connected to wires (not shown) that extend proximally to a energy source. When energy is provided to the conductive layer 210, segment 212 that is overlaid by conductive layer 210 is activated and changes to its stored curved shape. The activation is of sufficient force to steer the distal portion 204 of the member 202 in a direction opposite that of the segment which is activated, as illustrated in FIG. 7C. In certain embodiments, the segment can have a shape in its memory that would result in the catheter being steered in the direction that the segment lies.

In certain embodiments, the conductive layer 210 extends no more than about 90% around the perimeter (e.g., the circumference, when the sleeve 208 is in the form of a cylindrical tube) of the shape memory polymer sleeve 208 (e.g., no more than about 80%, no more than about 70%, no more than about 60%, no more than about 50%, or no more than about 40% around the perimeter of the shape memory polymer sleeve) and/or no less than about 30% around the perimeter of the shape memory polymer sleeve (e.g., no less than about 40%, no less than about 50%, no less than about 60%, no less than about 70%, or no less than about 80% around the perimeter of the shape memory polymer sleeve). In other embodiments, the conductive layer 210 can extend about 100% around the perimeter of the shape memory polymer sleeve 208. Steering is enabled by having the stored shape of the shape memory polymer sleeve 208 be curved, angled, or otherwise configured to change the direction of the catheter.

Other embodiments of steerable catheters can be formed. For example, FIGS. 8A and 8B show a steerable catheter 225 including a member 227 having a distal portion 229. A shape memory polymer sleeve 230 surrounds the distal portion 229 of the member 227. Shape memory polymer sleeve 230 is corrugated, much like a "paper lantern." A conductive layer 240 overlays (e.g., coats) a segment 232 of the shape memory polymer sleeve 230 that extends longitudinally for substantially the length of the shape memory polymer sleeve 230 and extends circumferentially around only a part of the shape memory polymer sleeve 230. When energy is provided to the conductive layer, segment 232 that is overlaid by conductive layer 240 is activated and changes to its stored substantially straight shape, such that the corrugations are straightened or flattened to a degree. The activation is of sufficient force to steer the distal portion 229 of the member 227 in a direction opposite that of the segment 232 which is activated, as illustrated in FIG. 8B. The corrugated nature of the opposite side of the shape memory polymer sleeve 230 is in certain embodiments sufficiently flexible to further corrugate, fold or coil itself and effectively shorten in overall length, aiding in the curvature of the member 227. In certain embodiments, the segment 232 can have a shape in its memory that would result in the catheter being steered in the direction that the segment 232 lies.

The shape memory polymer sleeve 230 in certain embodiments can be configured to facilitate or permit curvature of the sleeve, for example, by permitting or facilitating an increase and/or decrease in longitudinal length. For example, the sleeve can be cut into an expandable and/or contractible configuration (e.g., have relief openings extending around some or all of the circumference of the sleeve). The sleeve can have series of ridges to allow for flexion.

Figure 9A:
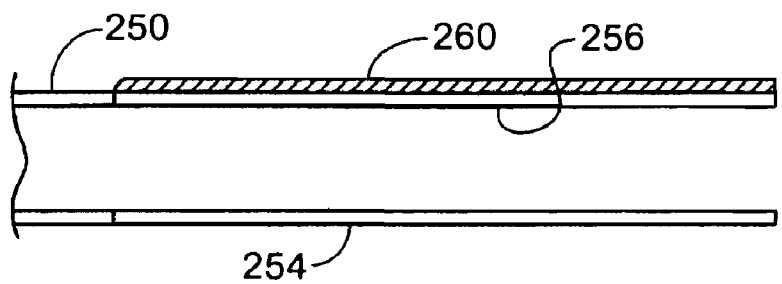
FIG. 9A is a detailed, cross-sectional view of an embodiment of a catheter including a shape memory polymer in a first state.
Figure 9B:
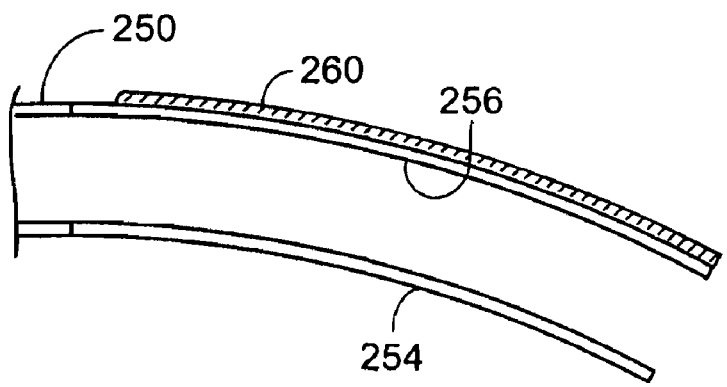
FIG. 9B is a cross-sectional view of the catheter of FIG. 9A, with the shape memory polymer in a second state.

In certain embodiments, a catheter includes a steering segment, located at or near the distal tip of the catheter, that includes a shape memory polymer having a conductive layer extending along a longitudinally extending portion of the steering segment but not extending around the circumference of the steering segment. The shape memory polymer elongates when activated, resulting in one portion of the circumference lengthening upon activation and forcing the catheter in a direction opposite that of the lengthened portion. For example, FIGS. 9A and 9B show a steerable catheter 250 having a distal portion 254 that includes a shape memory polymer. A conductive layer 260 overlays (e.g., coats) a segment 256 of the shape memory polymer of the distal portion 254 that extends longitudinally for substantially the length of distal portion 254 and extends around less than a full circumference of the distal portion 254. When energy is provided to the conductive layer, segment 256 that is overlaid by the conductive layer is activated and changes to its stored curved shape. The activation is of sufficient force to steer the distal portion 254 of catheter 250 in a direction opposite that of the segment which is activated, as illustrated in FIG. 9B. In certain embodiments, the segment can have a shape in its memory that would result in the catheter being steered in the direction that the segment lies.

The conductive layer in certain embodiments extends no more than about 90% around the perimeter of the distal portion (e.g., no more than about 80%, no more than about 70%, no more than about 60%, no more than about 50%, or no more than about 40% around the perimeter of the distal portion) and/or no less than about 30% around the perimeter of the distal portion (e.g., no less than about 40%, no less than about 50%, no less than about 60%, no less than about 70%, or no less than about 80% around the perimeter of the distal portion). In other embodiments, the conductive layer 210 can extend about 100% around the perimeter of the distal portion 254 that includes a shape memory polymer. Steering is enabled by having the stored shape of the shape memory polymer in the distal portion 254 be curved, angled, or otherwise configured to change the direction of the catheter.

Figure 10A:
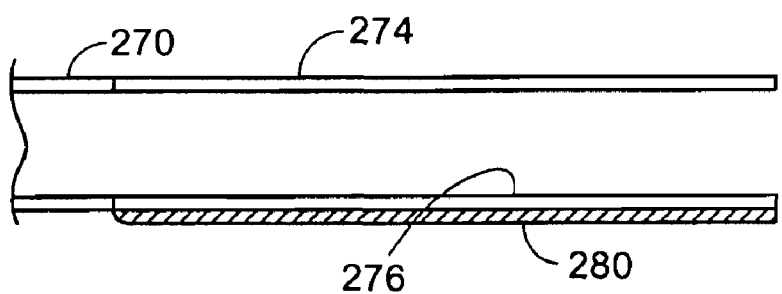
FIG. 10A is a detailed, cross-sectional view of an embodiment of a catheter including a shape memory polymer in a first state.
Figure 10B:
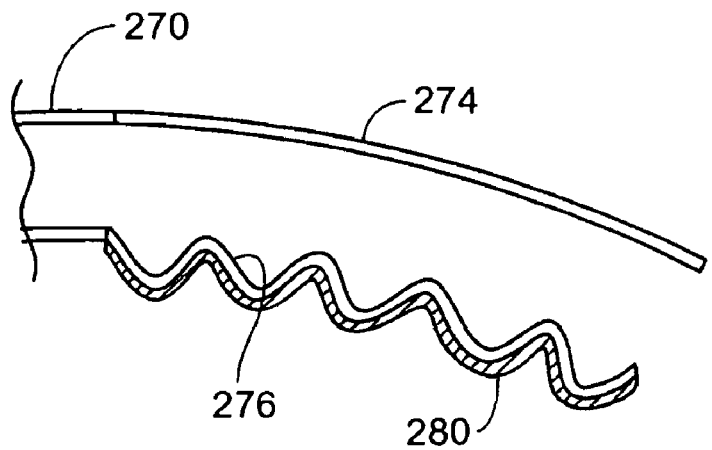
FIG. 10B is a cross-sectional view of the catheter of FIG. 10A, with the shape memory polymer in a second state.

FIGS. 10A and 10B show another embodiment of a steerable catheter 270 having a distal portion 274 that includes a shape memory polymer. A conductive layer 280 overlays (e.g., coats) a segment 276 of the distal portion 274 that extends longitudinally for substantially the length of distal portion 274 and extends around less than a full circumference of distal portion 274. When energy is provided to the conductive layer, segment 276 that is overlaid by the conductive layer 280 is activated and changes to its stored shape, which is corrugated, such that it effectively pulls the catheter tip towards segment 276.

Lumen Filter

Structures including shape memory polymer having conductive layers capable of activating selected part(s) of the shape memory polymer can also be used to form lumen filters. For example, as illustrated in FIGS. 11A-C, a lumen filter system 300 includes a shape memory polymer filter tube 310 having a first portion 312 with a conductive layer 320 on an outer surface 313 thereof, and a second portion 314 lacking a conductive layer on its outer surface 315. At least the first portion 312 of the shape memory polymer filter tube 310 is configured to permit fluid to pass while retaining particulate matter. For example, the first portion 312 of the shape memory polymer filter tube 310 can be formed into a screen, mesh, or other configuration having a plurality of openings through which fluid can flow. The openings can in certain embodiments be no larger than about 60 μm (e.g., no larger than about 50 μm, no larger than about 40 μm, or no larger than about 30 μm across) and/or no smaller than about 20 μm across (e.g., no smaller than about 30 μm, no smaller than about 40 μm, or no smaller than about 50 μm across). The shape memory polymer filter tube is disposed around a catheter 330 having a lumen 332 through which a vessel treatment device (not illustrated) can pass.

In use, the lumen filter system is introduced into a vessel lumen 340 of a vessel 342 and placed into a desired position, e.g., downstream, in terms of the direction of blood flow, from an obstruction 350 in vessel 342 (FIG. 11A). Upon being so positioned, energy can be provided to the conductive layer 320 (e.g., by wires, not shown) to activate the first portion 312 of the shape memory polymer filter tube 310, causing the first portion 312 to open outwardly into a roughly conical shape, illustrated in FIG. 11B, while the second portion 314 remains next to the catheter 330. Blood can flow through the holes in first portion 312 of the shape memory polymer filter tube 310. Optionally, a wire 360 having a distal tip 362 (e.g., configured to be able to bore through obstruction 350) can be introduced into the lumen 332 of catheter 330 and extended distally to extend out of a distal end 334 of catheter 330. Wire 360 can then be used to bore through obstruction 350, while the activated shape memory polymer filter tube collects obstruction particles 354 that are too large to pass through the holes in the shape memory polymer filter tube.

Once the obstruction 350 has been treated to the desired extent, e.g., once a passageway has been created of sufficient size to permit a stent delivery device to be passed into the obstruction for further treatment of the vessel, the provision of energy to conductive layer 320 can be ceased, and a second shape memory polymer structure (not shown) can be activated to change the lumen filter system back to its original shape, trapping the filtered obstruction particles 354, as illustrated in FIG. 11C. Lumen filter system 300, along with the entrapped obstruction particles 354, can then be removed from the vessel lumen 340.

Shape Memory Polymers

The devices described herein utilize a shape memory polymer, which is a polymeric material that can be in a first shape and can be activated by the impartation of energy to assume a second shape. In some embodiments, the energy for activation is thermal energy, whereby the polymer has a first shape at a first temperature, and can be activated to assume a different, second shape upon heating to a second temperature. In certain embodiments, the material can further assume a third shape upon heating to a third temperature higher than the second temperature.

The polymeric material can be natural, synthetic, or a mixture of natural and synthetic materials. In some embodiments, the polymeric material includes a natural polymer, e.g., zein, casein, gelatin, gluten, serum albumin, collagen, polysaccharides, polyhyaluronic acid, poly(3-hydroxyalkanoate)s, alginate, dextran, cellulose, collagen or mixtures of these polymers. In some embodiments, the polymeric material includes a synthetic polymer, e.g., chemical derivatives of collagen, chemical derivatives of cellulose, polyphosphazenes, poly(vinyl alcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyesters, degradable polymers, polyester amides, polyanhydrides, polycarbonates, polyorthoesters, polylactides, polyglycolides, polysiloxanes, polyurethanes, cellulose derivatives or mixtures of these polymers. In some embodiments, polymeric material includes mixtures of natural and synthetic polymers. In some embodiments, the polymeric material is cross-linked.

The polymer can be, for example, selected from polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and blends thereof.

In some embodiments, the first temperature is about room temperature (e.g., from about 15° C. to about 25° C., or from about 18° C. to about 21° C.), the second temperature is from about 37° C. to about 55° C. (e.g., from about 42° C. to about 50° C.).

Some polymers can have an elastic modulus of about 60,000 or 70,000 psi or more at 25° C. (ASTM D638M), e.g., from about 100,000 to about 250,000 or more, e.g., from about 250,000 to about 500,000 or more, e.g., from about 500,000 to about 1,000,000 or more.

Multi-Shape Memory Polymers

Figure 12:
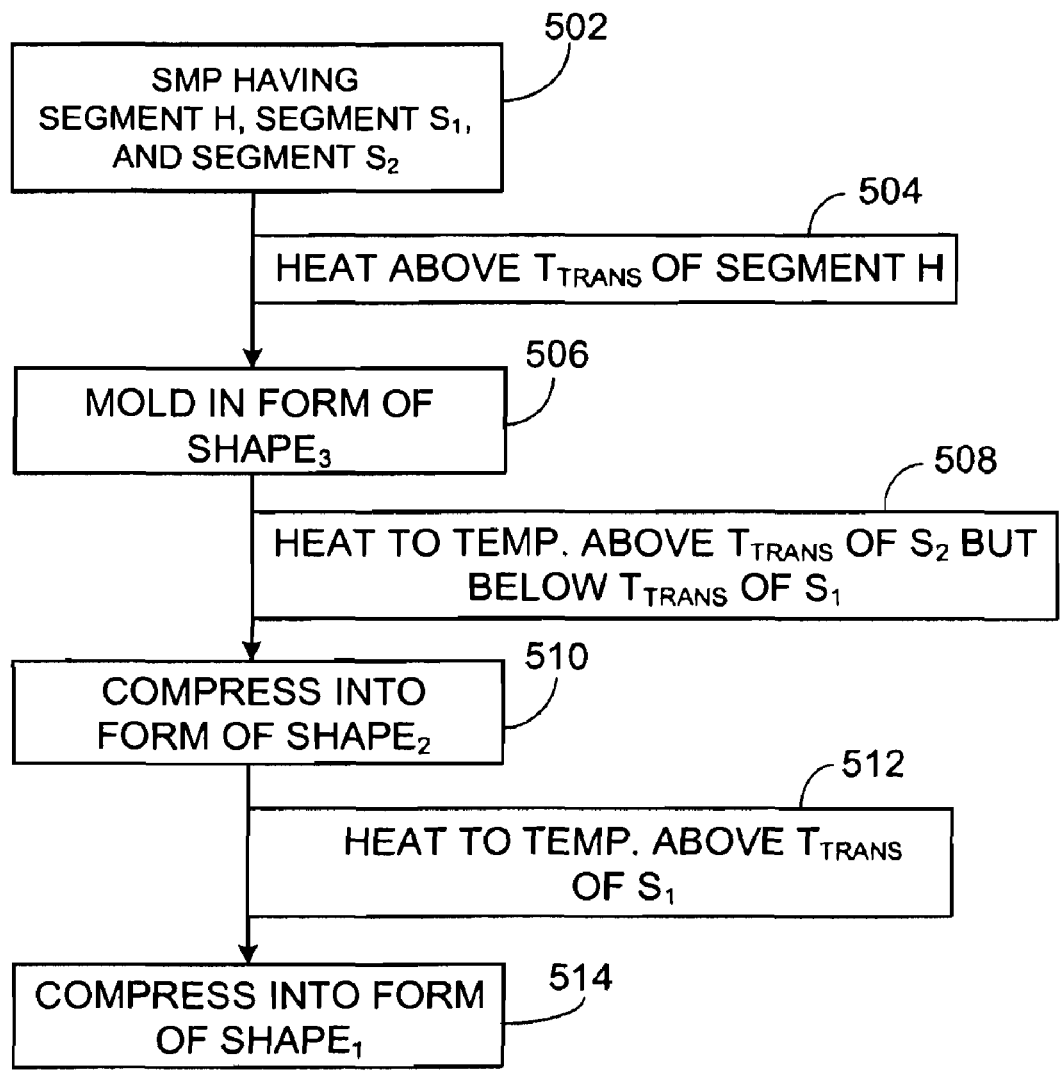
FIG. 12 is a flow chart of an embodiment of a method for imparting shape memories into a shape memory material.

In certain embodiments, the shape memory polymer is capable of storing multiple shapes within its memory, e.g., three, four, five, six or more different shapes. For example, a shape memory polymer that is capable of storing three shapes can include three distinct segments, each having a different transitional temperature. In some embodiments, such as that illustrated in FIG. 12, the polymeric material 502 of the shape memory polymer can include a hard segment (H) and two distinct soft segments ($S_1$ and $S_2$), wherein each segment has a different transitional temperature. The first soft segment ($S_1$) can have a $T_{trans}$ lower (e.g., at least 10° C. lower) than of the hard segment (H) and higher (e.g., at least 10° C. above) $T_{trans}$ of the second soft segment ($S_2$). The composition is heated in step 504 to a temperature above $T_{trans}$ of the hard segment (H') (e.g., is melted) and is shaped in step 506, e.g., extruded or molded, into the form of the third shape. This shape is stored by cooling to a first temperature below $T_{trans}$ of the hard segment (H') but above $T_{trans}$ the first soft segment ($S_1$). Heating the shape memory polymer (step 508) sleeve to a second temperature below that of $T_{trans}$ of the first soft segment ($S_1$), but above that of the second soft segment ($S_2$), enables shaping (step 510), e.g., by compression, into the form of the second shape. Heating (step 512) to a third temperature above $T_{trans}$ the second soft segment ($S_2$) enables shaping the sleeve (step 514) into the form of the first shape. In other embodiments, multiple layers of shape memory polymers with different transitional temperatures can also be used.

In use, the conductive layer heats only the portion of the shape memory polymer sleeve that contacts (and, to a lesser extent, portions immediately adjacent the point of contact). Energy is provided to the conductive layer to heat the coated portions of the shape memory polymer above $T_{trans}$ the second soft segment ($S_2$), at which point the Vans of coated portions change from the first shape to the second shape, e.g., a locked configuration. Further providing energy to the conductive layer heats the coated portions above $T_{trans}$ the first soft segment ($S_1$) and causes the shape memory polymer to Vans of transition from the second shape to the third shape, e.g., a locked configuration which provides channels for longitudinal fluid flow.

In other embodiments, a polymer blend of a first multiblock copolymer and a second multiblock copolymer can be utilized. The first multiblock copolymer includes a hard segment ($H_1$) with a relatively high transition temperature ($T_{trans}$) e.g., glass transition temperature or melting temperature, and a soft segment ($S'_1$) with a relatively low $T_{trans}$. The second multiblock copolymer includes a different hard segment ($H_2$) with a relatively low $T_{trans}$ and the same soft segment ($S'_1$) as in the first multiblock copolymer. Since the soft segments ($S'_1$) in both the first and second multiblock copolymers are identical, the polymers are miscible in each other. The resulting blend has three transition temperatures, one for the hard segment ($H_1$) of the a first multiblock copolymer, one for hard segment ($H_2$) of the second multiblock copolymer, and one for the soft segment ($S'_1$).

In certain embodiments, the first temperature is from about 40° C. to about 75° C. (e.g., from about 55° C. to about 70°

C.), the second temperature is from about 37° C. to about 55° C. (e.g., from about 42° C. to about 50° C.), and the third temperature is at about room temperature (e.g., from about 15° C. to about 25° C., or from about 18° C. to about 21° C.).

The polymers can be thermoplastic, thermoset, crystalline or amorphous. The polymers or portions of the polymers, e.g., a polymer segment or block, can be degradable, natural, or synthetic.

Natural polymers or polymer portions include, for example, zein, casein, gelatin, gluten, serum albumin, collagen, polysaccharides, polyhyaluronic acid, poly(3-hydroxyalkanoate)s, alginate, dextran, cellulose and collagen. Synthetic polymers or polymer portions include, for example, chemical derivatives of collagen, chemical derivatives of cellulose, polyphosphazenes, poly(vinyl alcohols), polyamides, polyacrylates, polyalkylenes, polyacrylamides, polyalkylene glycols, polyalkylene terephthalates, polyvinyl ethers, polyvinyl esters and polyvinyl halides, polyvinylpyrrolidone, polyesters. Degradable polymers or polymer portions include, for example, polyester amides, polyanhydrides, polycarbonates, polyorthoesters, polylactides, polyglycolides, polysiloxanes, polyurethanes and cellulose derivatives.

Generally, any of the above polymers can be cross-linked during their polymerization, or after their polymerization in a secondary step. The polymers can be cross-linked by application of radiation such as e-beam, UV, gamma, x-ray radiation or by heat-activated chemical crosslinking techniques, utilizing azo compounds or peroxides, e.g., organic peroxides, e.g., benzoyl peroxide. Radiation techniques provide the advantage that the polymer typically does not have to be substantially heated to achieve crosslinking. For e-beam radiation, an exposure of about 200-300, e.g. 250 kilograys, typically provides sufficient crosslinking.

Polymeric materials, e.g., homopolymers, block copolymers, and blends thereof, have also been described by Langer, U.S. Pat. Nos. 6,388,043 and 6,720,402, and in co-pending U.S. application Ser. No. 11/010,129, filed on Dec. 10, 2004, titled "Implantable Medical Devices, And Methods Of Delivering The Same", the contents of each of which is hereby incorporated by reference herein in its entirety.

Conductive Layers

The conductive layer is a film or layer of conductive material that is located on at least one surface of the shape memory polymer sleeve. The conductive layer receives energy and conducts the energy to the shape memory polymer that it contacts or overlays to activate the shape memory polymer. In certain embodiments, the conductive layer also serves to convert the energy it receives to a second type of energy that activates the shape memory polymer material. For example, the conductive layer in some embodiments receives electrical energy and converts that energy to heat, which is conducted to the shape memory polymer material and which activates the shape memory polymer material.

The conductive layer includes one or more conductive, for example, electrically and thermally conductive, materials. In some embodiments, the conductive material is not a shape memory material and/or superelastic. Exemplary materials include metals such as, e.g., gold, silver, platinum, tungsten, alloys of such metals, ceramics, carbon, and conductive inks. In certain embodiments, the conductive layer is a thin layer (e.g., no more than about 2, 1, 0.5, 0.2, or 0.1 mil thick) and is optionally flexible so as to maintain integrity when the shape memory polymer to which it is applied changes shape. In some embodiments, the conductive layer is applied to select portions of the shape memory polymer to activate less than 100% of the shape memory polymer (e.g., to activate no more than about 50%, 40%, 33%, 30%, 20%, or 10% of the shape memory polymer sleeve). Thus, the conductive layer can be configured such that less than the entirety (e.g., less than about 90%, 80%, 70%, 60%, 50%, 40%, 30%, 20%, or 10%) of the shape memory polymer is activated and changes shape.

Methods of Making

The shape memory polymer structures described herein can be formed by a variety of techniques. For example, the SMP structures can be formed by extrusion, co-extrusion, molding, e.g., injection molding, co-molding, compression molding, and/or casting. Apertures can be formed by laser ablation or by forming the apertures in the wall of the structure as the structure is molded. Where the structures are to be an integral part of a catheter or other device, the device can be formed by any of the above methods, or alternatively can be formed by attaching a shape memory polymer to a portion of a device such as a catheter, e.g., by adhesive or welding, such as butt welding.

The conductive layer can also be applied by a variety of techniques, such as, for example, sputter coating, plating, electroplating, electrostatic spraying, masking, pad printing, application of foils, hot-stamping, swaging or compressing rings or stamped parts to the sleeve, and/or through the application of micro-beads. The conductive layer can be applied to selected areas of the shape memory polymer structure to achieve desired activated shapes of the structure. In certain embodiments, the conductive layer has apertures, slots, or other cut-outs to allow for greater flexibility and/or expandability of the conductive layer.

In certain embodiments, an electrical contact is located in or on the conductive layer for attachment to an electrode. The electrode serves to transfer energy to the conductive layer from an energy source. In certain embodiments, the conductive coating is continuous, that is, the entire coating layer is interconnected to conduct energy from a single source throughout the conductive layer. The single electrode can serve to energize and activate multiple sections of the shape memory polymer. In other embodiments, multiple unconnected conductive layers can be utilized, with an electrode connected to each to separately energize each section. The conductive layers can also be insulated (e.g., with a non-conductive polymer or ceramic layer) to allow each layer to be selectively energize.

In certain embodiments, the conductive layer can include different conductive materials having differing degrees of conductivity. The different materials can be applied to different portions of the shape memory polymer and be interconnected such that energy can pass from one material to the alternate material. The materials may, for example, have differing degrees of resistance, and thus different rates of heating, such that energy can be provided by a single electrode for a period of time sufficient to activate the shape memory polymer overlaid by one of the different materials but not the shape memory polymer overlaid by the second conductive material, which may require more time to reach a sufficient heat to activate the shape memory polymer. Thus, a two-stage shape change can be achieved. The use of still different conductive materials can allow for three, four, five or more stage shape changes.

In some embodiments, the shape memory polymers are incorporated into a medical device, e.g., are made unitary with preexisting medical devices. For example, a catheter can be constructed that incorporated into the catheter material itself a section including a shape memory polymer having a conductive layer coating less than 100% of the shape memory polymer and thus capable of activating less than 100% of the shape memory polymer. In some embodiments, the shape memory polymer is a separate device that is incorporated into a catheter of other system, e.g., is placed between an inner catheter and an outer catheter of a concentric two-catheter system.

A number of embodiments have been described, but the invention is not so limited.

For example, in embodiments having more than one discrete SMP portion with a conductive layer thereon, the conductive layers can each have independent, individually-addressable wires attached to them to provide the energy for activating the shape memory polymer over which the conductive layer resides. Alternatively or additionally, multiple conductive layers can be interconnected by thin strips of conductive layer such that a single set of wires can energize multiple conductive layers.

Any of the locking mechanisms described above can include holes, slots, or other openings therein that, when the mechanism is in a locked configuration, permit fluid to pass from one side of the sleeve to the other. Alternatively or additionally, the sleeves can be configured to expand outwardly over less than the full circumference thereof, leaving channels or other locations for fluid to pass.

As another example, while in some embodiments the shape memory polymer structure has a pre-activation transverse cross-section that is circular, in some embodiments its transverse cross-section is non-circular. For example, the SMP structure can be elliptical or polygonal, e.g., square, pentagonal, hexagonal or octagonal. Similarly, the post-activated transverse cross-section of the activated portion of the shape memory polymer structure can be non-circular (e.g., elliptical or polygonal).

While in some embodiments the wall of the shape memory polymer structure includes only a single layer, in some embodiments, the wall includes more than one layer, e.g., 2, 3, 5 or 7 layers. Each layer may be made of the same material or each layer may be made of a different material.

While some structures have been shown that have a longitudinally constant wall thickness, in some embodiments, the wall thickness is longitudinally non-constant. Varying the wall thickness improves lateral flexibility which enables the structure, e.g., to be delivered through lumens and cavities with high curvature.

While some structures have been shown that have a transversely constant wall thickness, in some embodiments, the wall thickness is transversely non-constant.

While the shape memory polymer that are described above are activated by thermal energy, in certain embodiments, other forms of energy, e.g., light energy, can be utilized to activate the shape memory polymer. Where such is the case, the conductive layer will conduct the alternate form of energy or will convert energy provided to the conductive layer into the alternate form of energy.

While the shape memory polymer-containing elements have been described as sleeves, the shape memory polymer need not be in the form or shape of a sleeve, and can instead, e.g., form a part of a sleeve.

A shape memory polymer structure can include one or more portions having multiple sides contacting a conductive layer. For example, an SMP structure (such as the sleeves, filters and steerable catheters described above) can have a first side coated with a first conductive layer, and a second, opposing side coated with a second conductive layer.

The first and second conductive layers can be selectively activated to change the SMP structure from a first shape to a second shape, and back from the second shape to the first shape.

Still other embodiments are within the scope of the following claims.

What is claimed is:

1. A catheter comprising:
   an outer member;
   an inner member; and
   a structure located between the outer and inner members, the structure comprising a shape memory polymer and a conductive material on the shape memory polymer, wherein the structure is configured to be spaced from one of the outer member or the inner member at a first temperature, and to contact both the inner and outer members at a second temperature.

2. The catheter of claim 1, wherein at the first temperature, the structure is configured to abut the outer member and be spaced from the inner member, and at the second temperature, the structure is configured to couple the outer member to the inner member, thereby reducing movement of the outer member relative to the inner member.

3. The catheter of claim 1, wherein the structure is a sleeve and a diameter of a portion of the sleeve at the first temperature is larger than a diameter of the sleeve at the second temperature.

4. The catheter of claim 3, wherein the shape memory polymer includes a first portion, a second portion longitudinally adjacent the first portion, and a third portion longitudinally adjacent the second portion, wherein the conductive material is on the second portion only.

5. The catheter of claim 3, wherein the shape memory polymer comprises a first portion, a second portion longitudinally adjacent the first portion, and a third portion longitudinally adjacent the second portion, wherein the conductive material is on the first and third portions only.

6. The catheter of claim 5, wherein the second portion is secured to the outer member.

7. The catheter of claim 1, wherein at least a portion of the shape memory polymer is substantially circular in transverse cross-section at a first temperature and non-circular in transverse cross-section at a second temperature.

8. The catheter of claim 1, wherein the structure is a sleeve and the conductive material extends completely around a perimeter of the sleeve.

9. The catheter of claim 1, wherein the conductive member is connected to a conductor.

10. The catheter of claim 1, wherein the conductive material is selected from the group consisting of metals, alloys, ceramics, and graphite.

11. The catheter of claim 1, wherein the shape memory polymer comprises a polymer that is selected from the group consisting of natural polymers, zein, casein, gelatin, gluten, serum albumin, collagen, polysaccharides, polyhyaluronic acid, poly(3-hydroxyalkanoate)s, alginate, dextran, cellulose, collagen, synthetic polymers, chemical derivatives of collagen, chemical derivatives of cellulose, polyphosphazenes, poly(vinylalcohols), polyamides, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyesters, degradable polymers, polyester amides, polyanhydrides, polycarbonates, polyorthoesters, polylactides, polyglycolides, polysiloxanes, polyurethanes, cellulose derivatives, and mixtures thereof.

12. The catheter of claim 1, wherein the shape memory polymer comprises a polymer that is selected from the group consisting of polynorbomene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and blends thereof.

13. The catheter of claim 1, wherein the shape memory polymer comprises polycyclooctene.

14. A catheter comprising:
   an outer member;
   an inner member; and
   a structure located between the outer and inner members, the structure comprising a shape memory polymer and a conductive material on the shape memory polymer, wherein the shape memory polymer includes three or more segments, each segment having a different transitional temperature.

15. The catheter of claim 14, wherein the three or more segments are layers.

16. The catheter of claim 14, wherein each segment includes a multiblock copolymer.

17. The catheter of claim 14, wherein a first segment has a transitional temperature of from about 40° C to about 75° C, a second segment has a transitional temperature of from about 37° C to about 55° C, and a third segment has a transitional temperature of from about 15° C to about 25° C.

18. The catheter of claim 14, wherein the conductive material is selected from the group consisting of metals, alloys, ceramics, and graphite.

19. The catheter of claim 14, wherein the shape memory polymer comprises a polymer that is selected from the group consisting of polynorbornene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and blends thereof.

* * * * *

UNITED STATES PATENT AND TRADEMARK OFFICE
CERTIFICATE OF CORRECTION

| | | |
|---|---|---|
| PATENT NO. | : 8,377,038 B2 | Page 1 of 1 |
| APPLICATION NO. | : 13/271085 | |
| DATED | : February 19, 2013 | |
| INVENTOR(S) | : Tracee Eidenschink | |

It is certified that error appears in the above-identified patent and that said Letters Patent is hereby corrected as shown below:

In the Specification

Column 10, Line 20, delete "than of" and insert --than $T_{trans}$ of--.

Column 10, Line 27, delete "the first soft segment" and insert --of the first soft segment--.

Column 10, Line 33, delete "the second soft segment" and insert --of the second soft segment--.

Column 10, Line 42, delete "the second" and insert --of the second--.

Column 10, Line 43, delete "the Vans".

Column 10, Line 48, delete "Vans of".

Signed and Sealed this
Eleventh Day of June, 2013

Teresa Stanek Rea
*Acting Director of the United States Patent and Trademark Office*